United States Patent [19]
Chen

[11] Patent Number: 6,162,935
[45] Date of Patent: Dec. 19, 2000

[54] ANSA GROUP 4 METAL BIS (U-SUBSTITUTED) ALUMINUM METALLOCENES

[75] Inventor: Eugene Y. Chen, Midland, Mich.

[73] Assignee: The Dow Chemical Company, Midland, Mich.

[21] Appl. No.: 09/330,674

[22] Filed: Jun. 11, 1999

Related U.S. Application Data

[60] Provisional application No. 60/125,444, Mar. 22, 1999, provisional application No. 60/096,088, Aug. 11, 1998, provisional application No. 60/104,229, Oct. 14, 1998, provisional application No. 60/096,800, Aug. 17, 1998, and provisional application No. 60/100,490, Sep. 16, 1998.

[51] Int. Cl.$^7$ .............................. C07F 17/00; C07F 7/00; C08F 4/64
[52] U.S. Cl. .............................. 556/27; 556/52; 502/103; 502/153; 526/127; 526/160; 526/943
[58] Field of Search .................. 556/27, 52; 502/103, 502/153; 526/127, 160, 943

[56] References Cited

U.S. PATENT DOCUMENTS 3,274,223  9/1966  Feay ..................................... 260/429.5
5,721,185  2/1998  LaPointe ................................. 502/117

OTHER PUBLICATIONS

J. Am. Chem. Soc., 118, pp. 12451–12452, (1996).
J. Am. Soc. Chem. Commun., pp. 115–116, (1999).
Organometallics, 17, pp. 5908–5912, (1998).

Primary Examiner—Porfirio Nazario-Gonzalez

[57] ABSTRACT

Ansa bis($\mu$-substituted) Group 4 metal and aluminum compounds comprising a single Group 4 metal atom and two aluminum metal atoms corresponding to the formula:

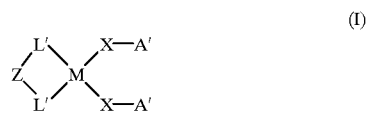

wherein:

L' is a π-bonded group,

M is a Group 4 metal,

Z is a divalent bridging group causing the complex to have an ansa structure,

X independently each occurrence is a Lewis basic ligand group able to form a $\mu$-bridging ligand group, and optionally the two X groups may be joined together, and A' independently each occurrence is an aluminum containing Lewis acid compound that forms an adduct with the metal complex by means of the $\mu$-bridging groups, and optionally two A' groups may be joined together thereby forming a single difunctional Lewis acid containing compound, and a method of preparation comprising contacting a charge-neutral metallocene of a Group 4 metal having at least two Lewis basic groups with at least two molar equivalents of a charge-neutral aluminum coordination complex having Lewis acidic aluminum atoms such that at least two of the aluminum atoms of the aluminum coordination complexes bond to at least two of the Lewis basic groups of the metallocene.

9 Claims, 1 Drawing Sheet

ANSA GROUP 4 METAL BIS (U-SUBSTITUTED) ALUMINUM METALLOCENES

CROSS-REFERENCE TO RELATED APPLICATION

This application claims priority benefit from provisional applications 60/125,444, filed Mar. 22, 1999, 60/096088, filed Aug. 11, 1998, 60/104,229, filed Oct. 14, 1998, 60/096800, filed Aug. 17, 1998 and 60/100490, filed Sep. 16, 1998.

BACKGROUND INFORMATION

The present invention relates to compounds that are useful as catalysts or catalyst components. More particularly, the present invention relates to such compounds comprising two aluminum and one Group 4 metal atoms that are particularly adapted for use in the coordination polymerization of unsaturated compounds. Such compounds are particularly advantageous for use in a polymerization process wherein at least one polymerizable monomer is combined under polymerization conditions with a catalyst or catalyst composition to form a polymeric product. In addition, the complexes of the current invention are especially useful in the production of steroregular polymers derived from α-olefins, especially isotactic polypropylene.

It is previously known in the art to activate Ziegler-Natta polymerization catalysts, particularly such catalysts comprising Group 3–10 metal complexes containing delocalized π-bonded ligand groups, by using Lewis acids to form catalytically active derivatives of such Group 3–10 metal complexes. Examples of suitable Lewis acids include tris(perfluorophenyl)borane and tris(perfluorobiphenyl)borane. Examples of such processes are disclosed in U.S. Pat. No. 5,721,185 and *J. Am. Chem. Soc.*, 118, 12451–12452 (1996), and elsewhere.

According to *J. Chem. Soc. Chem. Commun.*, 1999, 115–116, certain specifically substituted bis-Cp zirconocenedimethyl complexes may be converted to a dicationic derivative at −60° C. using multiple equivalents of trispentafluorophenylborane. The resulting metallocenes required the presence of either pendant phosphine moieties or benzyl groups on the cyclopentadienyl ring system and two equivalents of the methyltris(pentafluorophenyl)borate anion for charge balance. Upon heating even to −40° C. the product decomposed to give the corresponding monocationic complex and free tris(pentafluorophenyl)borane. Finally, in *Organometallics*, 1998,17, 5908–5912, the reaction of the strongly Lewis acidic compound, tris(pentafluorophenyl)aluminum, with bis(cyclopentadienyl) zirconium dimethyl was shown to form an unstable (μ-methyl) derivative via methide abstraction, which rapidly collapsed through a back exchange reaction at temperatures above 0° C. to form bis(cyclopentadienyl) methylpentafluorophenyl zirconium.

All of the foregoing attempts have failed to prepare a bis(μ-substituted) derivative of a metal complex that is stable at temperatures greater than 0° C. for a time sufficiently long for such compound to be useful in catalytic applications, especially in the polymerization of one or more ethylenically unsaturated monomers under addition polymerization conditions. Moreover, there is no known successful preparation of bis(μ-substituted)aluminum derivatives of a metal complex under any circumstances.

SUMMARY OF THE INVENTION

Figure 1:
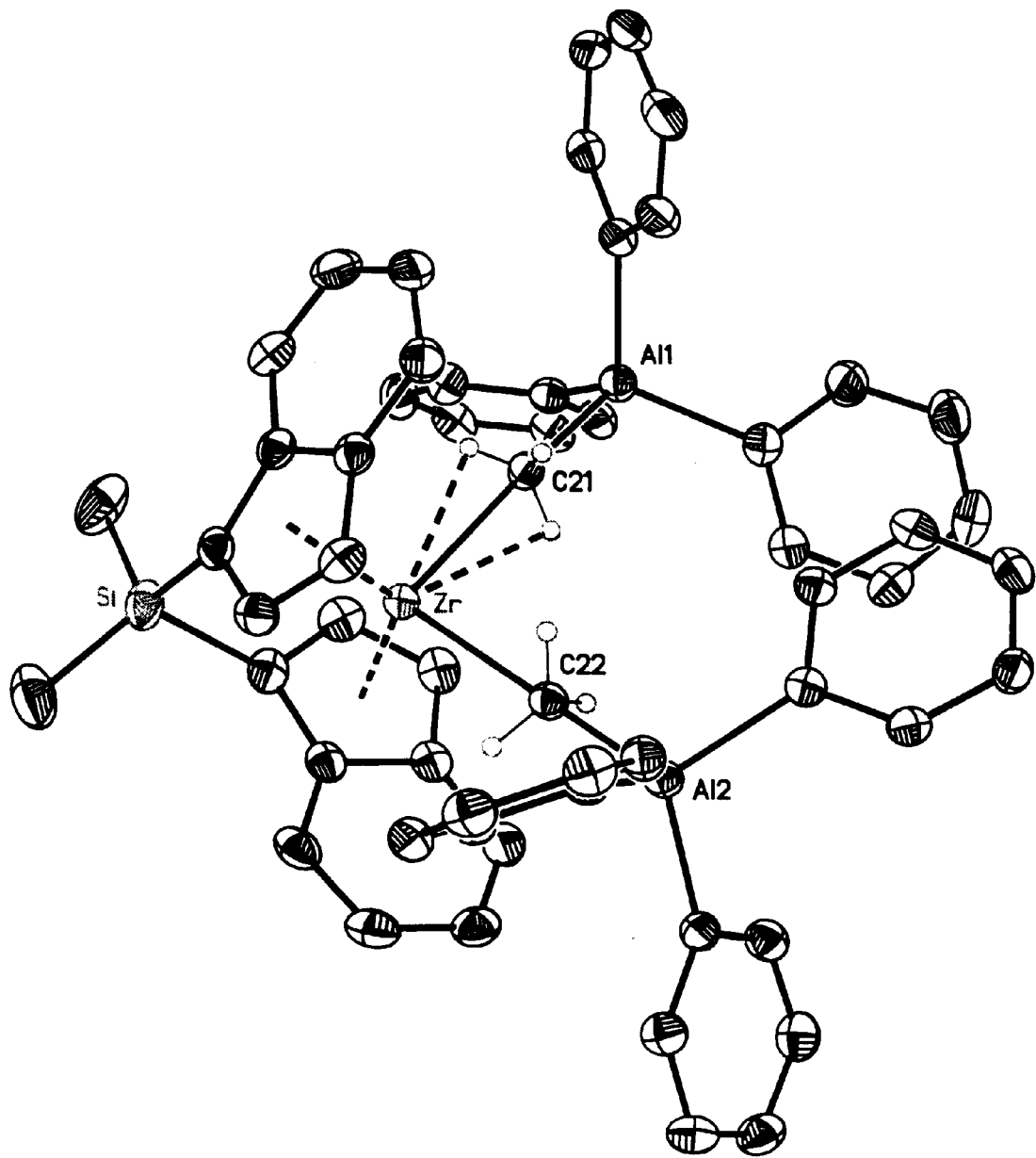
FIG. 1 is an ORTEP drawing based on the X-ray crystal analysis of the compound of Example 1.

According to the present invention there are now provided ansa bis(μ-substituted) Group 4 metal and aluminum metallocene compounds corresponding to the formula:

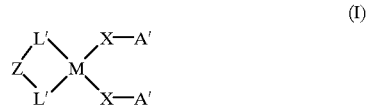

wherein:
L' independently each occurrence is a π-bonded group,
M is a Group 4 metal,
Z is a divalent bridging group causing the complex to have an ansa structure,
X independently each occurrence is a Lewis basic ligand group able to form a μ-bridging ligand group, and optionally the two X groups may be joined together, and
A' independently each occurrence is an aluminum containing Lewis acid compound that forms an adduct with the metal complex by means of the μ-bridging groups, and optionally two A' groups may be joined together thereby forming a single difunctional Lewis acid containing compound.

In the compounds of the invention, some or all of the bonds between M, X and A' may possess partial bond characteristics.

The compounds of the invention may be formed by contacting a charge-neutral Group IV metal coordination complex having at least two Lewis basic groups or precursor (s) thereof (catalyst) with at least two molar equivalents of a charge-neutral aluminum coordination complex having Lewis acidic aluminum atoms (activator) such that at least two of the aluminum atoms of the aluminum coordination complex bond to at least two of the Lewis basic groups of the Group IV metal coordination complex. Preferably the molar ratio of catalyst:activator is less than 1:100, more preferably the ratio is from 1:2.1 to 1:10, and most preferably from 1:3 to 1:8.

The present invented compounds are stable at elevated temperatures of at least 0° C., preferably at least 20° C. up to as high as 150° C. or higher and are usefully employed in a process for polymerization of ethylenically unsaturated monomers under solution, slurry, high pressure, or gas phase polymerization conditions. Relatively high molecular weight polymers may be readily obtained by use of the present metal complexes in the foregoing polymerization processes. Particularly, when employed in continuous solution or gas phase olefin polymerization processes, the present invented complexes may provide polymers having enhanced long chain branch incorporation and increased molecular weights.

Accordingly, the present invention additionally provides a process for the polymerization of one or more ethylenically unsaturated, polymerizable monomers comprising contacting the same, optionally in the presence of an inert aliphatic, alicyclic or aromatic hydrocarbon, under polymerization conditions with the above metal complex, or alternatively, forming the above metal complex in situ in the presence of or prior to addition to, a reaction mixture comprising one or more ethylenically unsaturated, polymerizable compounds.

DETAILED DESCRIPTION OF THE INVENTION

All references herein to elements belonging to a certain Group refer to the Periodic Table of the Elements published and copyrighted by CRC Press, Inc., 1995. Also any reference to the Group or Groups shall be to the Group or Groups as reflected in this Periodic Table of the Elements using the IUPAC system for numbering groups. Where any reference is made herein to any publication, patent application or provisional patent application, the contents thereof are incorporated herein in its entirety by reference. By the term "Lewis basic" and "Lewis acidic, in reference to ligand groups herein, is meant groups that are sufficiently nucleophilic or electrophilic respectively, such that the $\mu$-bridged complexes of the present invention are capable of formation. Preferred Lewis basic ligand groups, X, are hydrocarbyl, silyl, N,N-dialkylamido and alkanediylamido groups of up to 20 atoms not counting hydrogen, or two such X groups together are an alkanediyl or alkenediyl group which together with M form a metallocycloalkane or metallocycloalkene. Preferred Lewis acids are aluminum compounds containing at least one halohydrocarbyl ligand, preferably a fluoroaryl ligand. More preferred are tri(halohydrocarbyl) aluminum compounds having up to 50 atoms other than hydrogen, especially tri(fluoroaryl)aluminum compounds, most preferably tris(perfluoroaryl)aluminum compounds, and most highly preferably tris(pentafluorophenyl) aluminum. The Lewis acid may be used in pure form or in the form of an adduct with a Lewis base such as an ether.

Suitable aluminum containing Lewis acids may be prepared by exchange between tris(pentafluorophenyl)boron and alkylaluminum- or alkylaluminumoxy-compounds such as alumoxanes or diisobutyl(2,6-di-t-butyl-4-methylphenoxy)aluminum, as disclosed in Biagini et.al., U.S. Pat. No. 5,602,269, and provisional applications 60/096,088 and 60/104,229. The aluminum containing Lewis acids may be previously prepared and used in a relatively pure state or generated in situ by any of the foregoing techniques in the presence of the metal complex. Tris(perfluoroaryl)aluminum and exchange products obtained by mixing tris(perfluoroaryl)borane complexes with methylalumoxane (MAO) or trialkylaluminum-, especially, triisobutylaluminum-modified methylalumoxane (MMAO) are highly preferred. This reaction product with an alumoxane comprises a tris(fluoraryl)aluminum component of high Lewis acidity and a form of alumoxane which is rendered more Lewis acidic by the inherent removal of trimethylaluminum (TMA) via exchange to form trimethylborane. Optimized reaction products of this reaction correspond to the empirical formula:

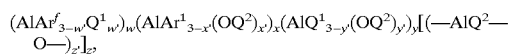

where;

Ar$^f$ is a fluorinated aromatic hydrocarbyl moiety of from 6 to 30 carbon atoms, preferably a perfluoroaryl group, and most preferably pentafluorophenyl;

Q$^1$ is C$_{1-20}$ alkyl, preferably methyl;

Q$^2$ is C$_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more Q$^2$ groups may be covalently linked with each other to form one or more fused rings or ring systems;

w' is a number from 0 to 3;

w is a number from 0 to 1.0; preferably from 0.5 to 1.0, more preferably from 0.8 to 1.0;

x' is a number from 0 to 3;

x is a number from 1.0 to 0; preferably from 0.5 to 0, more preferably from 0.2 to 0;

y' is a number from 0 to 3;

y is a number from 1.0 to 0; preferably from 0.5 to 0, more preferably from 0.2 to 0;

z' is a number from 0 to 30; and z is a number from 0 to 20, preferably from 0 to 5, more preferably from 0 to 0.5.

The moieties, (AlAr$^f$$_{3-w'}$Q$^1$$_{w'}$), (AlAr$^f$$_{3-x'}$(OQ$^2$)$_{x'}$), (AlQ$^1$$_{3-y'}$(OQ$^2$)$_{y'}$), and [(—AlQ$^2$—O—)$_{z'}$], may exist as discrete entities or as dynamic exchange products. That is, the foregoing formula is an idealized representation of the composition, which may actually exist in equilibrium with additional exchange products.

Preferably, L' is a cyclic or non-cyclic, aromatic or non-aromatic, anionic or neutral ligand group containing delocalized π-electrons capable of forming a bond with the Group 4 metal. Exemplary of such π-bonded groups are conjugated or nonconjugated, cyclic or non-cyclic diene and dienyl groups, allyl groups, boratabenzene groups, phosphole, and arene groups. Each atom in the delocalized π-bonded group may independently be substituted with a radical selected from the group consisting of hydrogen, halogen, hydrocarbyl, halohydrocarbyl, substituted heteroatom groups wherein the heteroatom is selected from Group 13–17 of the Periodic Table of the Elements, and the substituents are hydrocarbyl, silyl, hydrocarbylene, or another Group 13–17 heteroatom containing moiety, and optionally any of the foregoing hydrocarbyl, silyl, or hydrocarbylene substituents may be further substituted with a Group 13–17 heteroatom group. In addition two or more such radicals may together form a fused ring system, including partially or fully hydrogenated fused ring systems. Included within the term "hydrocarbyl" are C$_{1-20}$ straight, branched and cyclic alkyl or alkenyl radicals, C$_{6-20}$ aromatic radicals, C$_{7-20}$ alkyl-substituted aromatic radicals, and C$_{7-20}$ aryl-substituted alkyl radicals. Suitable heteroatom groups include alkoxy, aryloxy, dialkylamino, alkanediylamino, dialkylphosphino, silyl, germyl, and siloxy groups containing from 1 to 20 atoms not counting hydrogen. Examples include N,N-dimethylamino, pyrrolidinyl, trimethylsilyl, triethylsilyl, t-butyidimethylsilyl, methyldi(t-butyl)silyl, triphenylgermyl, and trimethylgermyl groups.

Examples of suitable anionic, delocalized π-bonded groups include cyclopentadienyl, indenyl, fluorenyl, tetrahydroindenyl, tetrahydrofluorenyl, octahydrofluorenyl, pentadienyl, cyclohexadienyl, dihydroanthracenyl, hexahydroanthracenyl, decahydroanthracenyl groups, indacenyl, cyclopenta(l)phenanthrenyl, and boratabenzene groups, as well as C$_{1-10}$ hydrocarbyl-, C$_{1-10}$ halohydrocarbyl-, C$_{1-10}$ amido-, or C$_{1-10}$ hydrocarbylsilyl-substituted derivatives thereof.

The boratabenzenes are anionic ligands that are boron-containing analogues to benzene. They are previously known in the art having been described by G. Herberich, et al., in *Organometallics*, 14,1, 471–480 (1995). Preferred boratabenzenes correspond to the formula:

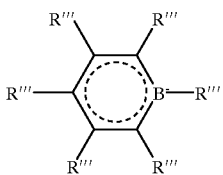

wherein R''' in one occurrence is a covalent bond to Z, and in each remaining occurrence R''' is independently, hydrogen or a hydrocarbyl, silyl, N,N-dihydrocarbylamino, hydrocarbadiylamino, or germyl group, said R''' having up to 20 atoms not counting hydrogen, and optionally one or more R''' groups may be bonded together forming a multicyclic fused ring system.

Phospholes are anionic ligands that are phosphorus-containing analogues to a cyclopentadienyl group. They are previously known in the art having been described by WO 98/50392, and elsewhere. Preferred phosphole ligands correspond to the formula:

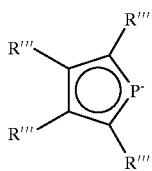

wherein R''' is as previously defined.

A preferred class of such Group 4 metal metallocenes used according to the present invention and the resulting compounds of the invention respectively correspond to the formulae:

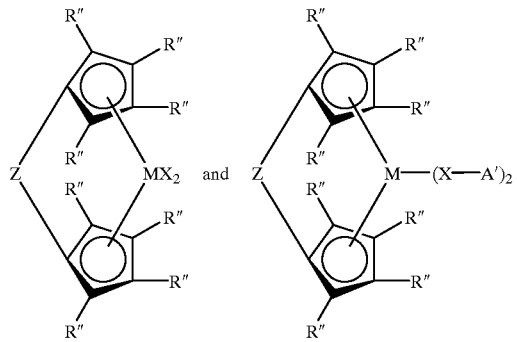

wherein:
R'' in each occurrence independently is selected from the group consisting of hydrogen, hydrocarbyl, silyl, halohydrocarbyl, N,N-dialkylamino, and alkanediylamino, said R'' having up to 20 atoms, not counting hydrogen, or adjacent R'' groups are joined together thereby forming a fused ring system, X independently each occurrence is hydrocarbyl, or two X groups together are an alkanediyl or alkenediyl group, said X having up to 20 atoms not counting hydrogen;

Z is $SiR^*_2$, $CR^*_2$, $SiR^*_2SiR^*_2$, $CR^*_2CR^*_2$, $CR^*=CR^*$, $CR^*_2SiR^*_2$, $BOR^*$, $BNR^*_2$, or $GeR^*_2$, wherein $R^*$ independently each occurrence is $C_{1-4}$ alkyl or $C_{6-10}$ aryl, or optionally two $R^*$ groups are joined together; and M, and A' are as previously defined.

More preferred anionic delocalized π-bonded groups, L', are cyclopentadienyl, tetramethylcyclopentadienyl, indenyl, 2,3-dimethylindenyl, fluorenyl, 2-methylindenyl, 2-methyl-4-phenylindenyl, 3-dimethylaminoindenyl, 3-pyrrolidinoindenyl, 3-piperidinoindenyl, 2-methyl-4-(3,5-bis(trifluoromethyl)phenyl)inden-1-yl, 2,4,6,7-tetramethylinden-1-yl, 2-methyl-4-(1-naphthyl)indene-1-yl, 3,4-cyclopenta(1)phenanthrenyl, 2,3-cyclopenta(1)phenanthrenyl, 2-methyl-4,5-benzoinden-1-yl tetrahydrofluorenyl, octahydrofluorenyl, 1-indacenyl, 3,4-(cyclopenta(l)phenanthren-1-yl), and tetrahydroindenyl.

Most preferred Group 4 metal complexes used according to the present invention and the resulting compounds of the invention respectively correspond to the formulae:

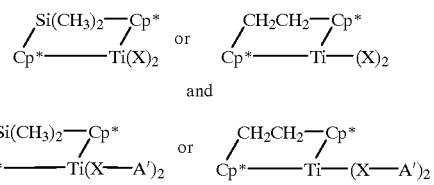

wherein:
Cp* is tetramethylcyclopentadienyl, 2-methyl-4-phenylinden-1-yl, 3-pyrrolidinoinden-1-yl, 1-indacenyl, or 3,4-(cyclopenta(l)phenanthren-1-yl);
X is methyl; and
A' is tris(pentafluorophenyl)aluminum.

Examples of charge neutral metal complexes which may be used to prepare the compounds of the invention include:
rac-dimethylsilanebis(cyclopentadienyl)zirconium dimethyl,
rac-dimethylsilanebis(3-(t-butyl)cyclopentadien-1-yl) zirconium dimethyl,
rac-dimethylsilanebis(tetramethylcyclopentadienyl) zirconium dimethyl,
rac-dimethylsilanebis(inden-1-yl)zirconium dimethyl,
rac-dimethylsilanebis(hexamethylinden-1-yl)zirconium dimethyl,
rac-dimethylsilanebis(2-methyl-4-phenylinden-1-yl) zirconium dimethyl,
rac-dimethylsilanebis(3-(N-pyrrolidino)inden-1-yl) zirconium dimethyl,
rac-dimethylsilanebis(s-indacen-1-yl)zirconium dimethyl,
rac-dimethylsilanebis(3,4-(cyclopenta(l)phenanthren-1-yl)) zirconium dimethyl,
rac-dimethylsilanebis(cyclopentadienyl)zirconium 2,3-dimethyl-2-butene-1,4-diyl,
rac-dimethylsilanebis(3-(t-butyl)cyclopentadien-1-yl) zirconium 2,3-dimethyl-2-butene-1,4-diyl,
rac-dimethylsilanebis(tetramethylcyclopentadienyl) zirconium 2,3-dimethyl-2-butene-1,4-diyl,
rac-dimethylsilanebis(inden-1-yl)zirconium 2,3-dimethyl-2-butene-1,4-diyl,
rac-dimethylsilanebis(hexamethylinden-1-yl)zirconium 2,3-dimethyl-2-butene-1,4-diyl,
rac-dimethylsilanebis(2-methyl-4-phenylinden-1-yl) zirconium 2,3-dimethyl-2-butene-1,4-diyl,
rac-dimethylsilanebis(3-(N-pyrrolidino)inden-1-yl) zirconium 2,3-dimethyl-2-butene-1,4-diyl,
rac-dimethylsilanebis(s-indacen-1-yl)zirconium 2,3-dimethyl-2-butene-1,4-diyl,
rac-dimethylsilanebis(3,4-(cyclopenta(l)phenanthren-1-yl)) zirconium 2,3-dimethyl-2-butene-1,4-diyl, rac-1,2-ethanebis(cyclopentadienyl)zirconium dimethyl,
rac-1,2-ethanebis(3-(t-butyl)cyclopentadien-1-yl)zirconium dimethyl,
rac-1,2-ethanebis(tetramethylcyclopentadienyl)zirconium dimethyl,
rac-1,2-ethanebis(inden-1-yl)zirconium dimethyl,
rac-1,2-ethanebis(hexamethylinden-1-yl)zirconium dimethyl,
rac-1,2-ethanebis(2-methyl-4-phenylinden-1-yl)zirconium dimethyl,
rac-1,2-ethanebis(3-(N-pyrrolidino)inden-1-yl)zirconium dimethyl,
rac-1,2-ethanebis(s-indacen-1-yl)zirconium dimethyl,
rac-1,2-ethanebis(3,4-(cyclopenta(l)phenanthren-1-yl))zirconium dimethyl,
rac-1,2-ethanebis(cyclopentadienyl)zirconium 2,3-dimethyl-2-butene-1,4-diyl,
rac-1,2-ethanebis(3-(t-butyl)cyclopentadien-1-yl)zirconium 2,3-dimethyl-2-butene-1,4-diyl,
rac-1,2-ethanebis(tetramethylcyclopentadienyl)zirconium 2,3-dimethyl-2-butene-1,4-diyl,
rac-1,2-ethanebis(inden-1-yl)zirconium 2,3-dimethyl-2-butene-1,4-diyl,
rac-1,2-ethanebis(hexamethylinden-1-yl)zirconium 2,3-dimethyl-2-butene-1,4-diyl,
rac-1,2-ethanebis(2-methyl-4-phenylinden-1-yl)zirconium 2,3-dimethyl-2-butene-1,4-diyl,
rac-1,2-ethanebis(3-(N-pyrrolidino)inden-1-yl)zirconium 2,3-dimethyl-2-butene-1,4-diyl,
rac-1,2-ethanebis(s-indacen-1-yl)zirconium 2,3-dimethyl-2-butene-1,4-diyl, and
rac-1,2-ethanebis(3,4-(cyclopenta(l)phenanthren-1-yl))zirconium 2,3-dimethyl-2-butene-1,4-diyl.

Examples of ansa bis($\mu$-substituted) Group 4 metal and aluminum metallocene compounds of the invention include the following:
rac-dimethylsilanebis(cyclopentadienyl)zirconium $\mu$-(dimethyl)bis(tris(pentafluorophenyl)aluminum),
rac-dimethylsilanebis(3-(t-butyl)cyclopentadien-1-yl)zirconium $\mu$-(dimethyl)bis(tris(pentafluorophenyl)aluminum),
rac-dimethylsilanebis(tetramethylcyclopentadienyl)zirconium $\mu$-(dimethyl)bis(tris(pentafluorophenyl)aluminum),
rac-dimethylsilanebis(inden-1-yl)zirconium $\mu$-(dimethyl)bis(tris(pentafluorophenyl)aluminum),
rac-dimethylsilanebis(hexamethylinden-1-yl)zirconium $\mu$-(dimethyl)bis(tris(pentafluorophenyl)aluminum),
rac-dimethylsilanebis(2-methyl-4-phenylinden-1-yl)zirconium $\mu$-(dimethyl)bis(tris(pentafluorophenyl)aluminum),
rac-dimethylsilanebis(3-(N-pyrrolidino)inden-1-yl)zirconium $\mu$-(dimethyl)bis(tris(pentafluorophenyl)aluminum),
rac-dimethylsilanebis(s-indacen-1-yl)zirconium $\mu$-(dimethyl)bis(tris(pentafluorophenyl)aluminum),
rac-dimethylsilanebis(3,4-(cyclopenta(l)phenanthren-1-yl))zirconium $\mu$-(dimethyl)bis(tris(pentafluorophenyl)aluminum),
rac-dimethylsilanebis(cyclopentadienyl)zirconium $\mu$(2,3-dimethyl-2-butene-1,4-)bis(tris(pentafluorophenyl)aluminum),
rac-dimethylsilanebis(3-(t-butyl)cyclopentadien-1-yl)zirconium $\mu$-(2,3-dimethyl-2-butene-1,4-bis(tris(pentafluorophenyl)aluminum),
rac-dimethylsilanebis(tetramethylcyclopentadienyl)zirconium $\mu$-(2,3-dimethyl-2-butene-1,4-bis(tris(pentafluorophenyl)aluminum),
rac-dimethylsilanebis(inden-1-yl)zirconium $\mu$-(2,3-dimethyl-2-butene-1,4-bis(tris(pentafluorophenyl)aluminum),
rac-dimethylsilanebis(hexamethylinden-1-yl)zirconium $\mu$-(2,3-dimethyl-2-butene-1,4-bis(tris(pentafluorophenyl)aluminum),
rac-dimethylsilanebis(2-methyl-4-phenylinden-1-yl)zirconium $\mu$-(2,3-dimethyl-2-butene-1,4-bis(tris(pentafluorophenyl)aluminum),
rac-dimethylsilanebis(3-(N-pyrrolidino)inden-1-yl)zirconium $\mu$-(2,3-dimethyl-2-butene-1,4-bis(tris(pentafluorophenyl)aluminum),
rac-dimethylsilanebis(s-indacen-1-yl)zirconium $\mu$-(2,3-dimethyl-2-butene-1,4-bis(tris(pentafluorophenyl)aluminum),
rac-dimethylsilanebis(3,4-(cyclopenta(l)phenanthren-1-yl))zirconium $\mu$-(2,3-dimethyl-2-butene-1,4-bis(tris(pentafluorophenyl)aluminum),
rac-1,2-ethanebis(cyclopentadienyl)zirconium $\mu$-(dimethyl)bis(tris(pentafluorophenyl)aluminum),
rac-1,2-ethanebis(3-(t-butyl)cyclopentadien-1-yl)zirconium $\mu$-(dimethyl)bis(tris(pentafluorophenyl)aluminum),
rac-1,2-ethanebis(tetramethylcyclopentadienyl)zirconium $\mu$-(dimethyl)bis(tris(pentafluorophenyl)aluminum),
rac-1,2-ethanebis(inden-1-yl)zirconium $\mu$-(dimethyl)bis(tris(pentafluorophenyl)aluminum),
rac-1,2-ethanebis(hexamethylinden-1-yl)zirconium $\mu$-(dimethyl)bis(tris(pentafluorophenyl)aluminum),
rac-1,2-ethanebis(2-methyl-4-phenylinden-1-yl)zirconium $\mu$-(dimethyl)bis(tris(pentafluorophenyl)aluminum),
rac-1,2-ethanebis(3-(N-pyrrolidino)inden-1-yl)zirconium $\mu$-(dimethyl)bis(tris(pentafluorophenyl)aluminum),
rac-1,2-ethanebis(s-indacen-1-yl)zirconium $\mu$-(dimethyl)bis(tris(pentafluorophenyl)aluminum),
rac-1,2-ethanebis(3,4-(cyclopenta(l)phenanthren-1-yl))zirconium $\mu$-(dimethyl)bis(tris(pentafluorophenyl)aluminum),
rac-1,2-ethanebis(cyclopentadienyl)zirconium $\mu$-(2,3-dimethyl-2-butene-1,4-bis(tris(pentafluorophenyl)aluminum),
rac-1,2-ethanebis(3-(t-butyl)cyclopentadien-1-yl)zirconium $\mu$-(2,3-dimethyl-2-butene-1,4-bis(tris(pentafluorophenyl)aluminum),
rac-1,2-ethanebis(tetramethylcyclopentadienyl)zirconium $\mu$-(2,3-dimethyl-2-butene-1,4-bis(tris(pentafluorophenyl)aluminum),
rac-1,2-ethanebis(inden-1-yl)zirconium $\mu$-(2,3-dimethyl-2-butene-1,4-bis(tris(pentafluorophenyl)aluminum),
rac-1,2-ethanebis(hexamethylinden-1-yl)zirconium $\mu$-(2,3-dimethyl-2-butene-1,4-bis(tris(pentafluorophenyl)aluminum),
rac-1,2-ethanebis(2-methyl-4-phenylinden-1-yl)zirconium $\mu$-(2,3-dimethyl-2-butene-1,4-bis(tris(pentafluorophenyl)aluminum),
rac-1,2-ethanebis(3-(N-pyrrolidino)inden-1-yl)zirconium $\mu$-(2,3-dimethyl-2-butene-1,4-bis(tris(pentafluorophenyl)aluminum),
rac-1,2-ethanebis(s-indacen-1-yl)zirconium $\mu$-(2,3-dimethyl-2-butene-1,4-bis(tris(pentafluorophenyl)aluminum) and
rac-1,2-ethanebis(3,4-(cyclopenta(l)phenanthren-1-yl))zirconium $\mu$-(2,3-dimethyl-2-butene-1,4-bis(tris(pentafluorophenyl)aluminum).

The metal complexes are prepared in one embodiment by reacting an aluminum containing Lewis acid compound with an ansa Group 4 metallocene, the molar ratio of Lewis acid compound to ansa metallocene being at least 2:1, preferably from 2:1 to 5:1, most preferably from 2:1 to 2.5:1. The foregoing process may be illustrated by the following reaction scheme:

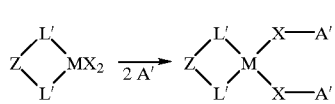
(I)

wherein:
L', M, X, and A' are as previously defined.
Preferably,
M is zirconium or hafnium, most preferably zirconium;
X independently each occurrence is a monovalent hydrocarbyl or silyl group, a trihydrocarbylsilyl-, trihydrocarbylgermyl- or halo-substituted derivative thereof, a N,N-dihydrocarbylamido group or a hydrocarbadiylamido group, said X containing up to 20 atoms not counting hydrogen, and optionally two X groups may be bound together; and
A' corresponds to the empirical formula:

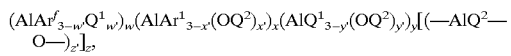

where;
$Ar^f$ is as previously defined, preferably fluoroaryl, more preferably perfluoroaryl, and most preferably pentafluorophenyl;
$Q^1$ is $C_{1-20}$ alkyl, preferably methyl;
$Q^2$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^2$ groups may be covalently linked with each other to form one or more fused rings or ring systems;
w' is a number from 0 to 3;
w is a number from 0 to 1.0; preferably from 0.5 to 1.0, more preferably from 0.8 to 1.0;
x' is a number from 0 to 3;
x is a number from 1.0 to 0; preferably from 0.5 to 0, more preferably from 0.2 to 0;
y' is a number from 0 to 3;
y is a number from 1.0 to 0; preferably from 0.5 to 0, more preferably from 0.2 to 0;
z' is a number from 0 to 20; and
z is a number from 0 to 20, preferably from 0 to 5, more preferably from 0 to 0.5.
Most preferably, A' is

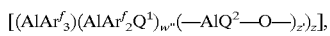

where,
w'' is a number from 0 to 0.5, preferably from 0 to 0.1, more preferably from 0 to 0.01; and
$Ar^1$, $Q^1$, $Q^2$, z' and z are as previously defined.
Most preferably A' is $AlAr^f_3$, wherein $Ar^f$ is perfluorophenyl.
The process is conducted at temperatures from −80 to 220° C., preferably from 25 to 50° C., and preferably in a hydrocarbon diluent or solvent, especially $C_{4-12}$ aliphatic, cycloaliphatic or aromatic hydrocarbons or a mixture thereof. The initially formed compound (I) in solution may convert by means of an intermolecular rearrangement over time to several additional complexes, primarily through replacement of the μ-methyl group with a ligand group from the Lewis acid, for example, pentafluorophenyl. Such a rearrangement is generally relatively slow at moderate temperatures up to 150° C. At 25° C. compound (I) generally possesses a half life of about 2 hours. Solvent free crystals of Compound (I) are relatively stable when retained under inert atmosphere.

The term "stable" as used herein refers to metal complexes having sufficient lifetimes to provide useful quantities of polymer under use conditions. The conversion products are not necessarily lacking in utility, and in fact, may be active catalyst species or necessary intermediates thereto. One measure of the stability of the present complexes is the determination of the compound's half-life under given environmental conditions. The time in which one half of a given product is converted to a different compound or compounds can often be measured. Preferred stable compounds are further quantified as those compounds having a half-life of at least 1 second at a temperature greater than 0° C.

Since two M-X bonds are potentially available for activation in the complexes, it is believed, without wishing to be bound by such belief, that under actual polymerization conditions, two polymer chains may propagate simultaneously or approximately simultaneously during polymerizations using the foregoing complexes, thereby providing greater potential for β-hydride elimination and α-olefin macromer reincorporation into the growing polymer chains under actual use conditions. Alternatively, the two μ-bridging moieties may interact, particularly where the Lewis acid groups are relatively labile, to produce a single, highly active polymerization site.

Suitable addition polymerizable monomers for use with the foregoing novel catalyst compositions include ethylenically unsaturated monomers, acetylenic compounds, conjugated or non-conjugated dienes, and polyenes. Preferred monomers include olefins, for example alpha-olefins having from 2 to 20,000, preferably from 2 to 20, more preferably from 2 to 8 carbon atoms and combinations of two or more of such alpha-olefins. Particularly suitable alpha-olefins include, for example, ethylene, propylene, 1-butene, isobutylene, 1-pentene, 4-methylpentene-1, 1-hexene, 1-heptene, 1-octene, 1-nonene, 1-decene, 1-undecene, 1-dodecene, 1-tridecene, 1-tetradecene, 1-pentadecene, or combinations thereof, as well as long chain vinyl terminated oligomeric or polymeric reaction products formed during the polymerization, and $C_{10-30}$ α-olefins specifically added to the reaction mixture in order to produce relatively long chain branches in the resulting polymers. Preferably, the alpha-olefins are ethylene, propylene, 1-butene, 1-pentene, 4-methyl-pentene-1, 1-hexene, 1-octene, and combinations of ethylene and/or propene with one or more other alpha-olefins. Other preferred monomers include styrene, halo- or alkyl substituted styrenes, vinylbenzocyclobutene, 1,4-hexadiene, dicyclopentadiene, ethylidene norbornene, and 1,7-octadiene. Mixtures of the above-mentioned monomers may also be employed.

In a further embodiment, the invention comprises a process for the polymerization of α-olefins comprising contacting one or more α-olefins with a catalyst composition comprising:

1) a group 4 metal complex corresponding to the formula:

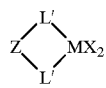

wherein, Z, L', M, and X are as previously defined with respect to formula I; and 2) tris(perfluorophenyl)aluminum, wherein the equivalent ratio of metal complex: tris(perfluorophenyl)aluminum is from 1:2 to 1:5. The polymerization efficiency of the process is desirably at least twice, more preferably at least three times the efficiency of a comparable polymerization wherein the equivalent ratio of group 4 metal complex:tris(perfluorophenyl)aluminum is 1:1.

In general, the polymerization may be accomplished under conditions well known in the prior art for Ziegler-Natta or Kaminsky-Sinn type polymerization reactions. Suspension, solution, slurry, gas phase or high pressure, whether employed in batch or continuous form or other process conditions, may be employed if desired. Examples of such well known polymerization processes are depicted in WO 88/02009, U.S. Pat. Nos. 5,084,534, 5,405,922, 4,588,790, 5,032,652, 4,543,399, 4,564,647, 4,522,987, and elsewhere. Preferred polymerization temperatures are from 0–250° C. Preferred polymerization pressures are from atmospheric to 3000 atmospheres.

Preferred processing conditions include solution polymerization, more preferably continuous solution polymerization processes, conducted in the presence of an aliphatic or alicyclic liquid diluent. By the term "continuous polymerization" is meant that at least the products of the polymerization are continuously removed from the reaction mixture. Preferably one or more reactants are also continuously added to the polymerization mixture during the polymerization. Examples of suitable aliphatic or alicyclic liquid diluents include straight and branched-chain $C_{4-12}$ hydrocarbons and mixtures thereof; alicyclic hydrocarbons such as cyclohexane, cycloheptane, methylcyclohexane, methylcycloheptane, and mixtures thereof; and perfluorinated hydrocarbons such as perfluorinated $C_{4-10}$ alkanes, and the like. Suitable diluents also include aromatic hydrocarbons (particularly for use with aromatic $\alpha$-olefins such as styrene or ring alkyl-substituted styrenes) including toluene, ethylbenzene or xylene, as well as liquid olefins (which may act as monomers or comonomers) including ethylene, propylene, 1-butene, isobutylene, butadiene, 1-pentene, cyclopentene, 1-hexene, cyclohexene, 3-methyl-1-pentene, 4-methyl-1-pentene, 1,4-hexadiene, 1-octene, 1-decene, styrene, divinylbenzene, allylbenzene, vinyltoluene (including all isomers alone or in admixture), and the like. Mixtures of the foregoing are also suitable. The foregoing diluents may also be advantageously employed during the synthesis of the metal complexes and catalyst activators of the present invention.

In most polymerization reactions the molar ratio of catalyst:polymerizable compounds employed is from $10^{-12}$:1 to $10^{-1}$:1, more preferably from $10^{-12}$:1 to $10^{-5}$:1.

Molecular weight control agents can be used in combination with the present cocatalysts. Examples of such molecular weight control agents include hydrogen, trialkyl aluminum compounds or other known chain transfer agents. A particular benefit of the use of the present cocatalysts is the ability (depending on reaction conditions) to produce narrow molecular weight distribution $\alpha$-olefin homopolymers and copolymers in greatly improved catalyst efficiencies. Preferred polymers have Mw/Mn of less than 2.5, more preferably less than 2.3. Such narrow molecular weight distribution polymer products are highly desirable due to improved tensile strength properties.

The catalyst composition of the present invention can also be employed to advantage in the gas phase polymerization and copolymerization of olefins, preferably by supporting the catalyst composition by any suitable technique. Gas phase processes for the polymerization of olefins, especially the homopolymerization and copolymerization of ethylene and propylene, and the copolymerization of ethylene with higher alpha olefins such as, for example, 1-butene, 1-hexene, 4-methyl-1-pentene are well known in the art. Such processes are used commercially on a large scale for the manufacture of high density polyethylene (HDPE), medium density polyethylene (MDPE), linear low density polyethylene (LLDPE) and polypropylene.

The gas phase process employed can be, for example, of the type which employs a mechanically stirred bed or a gas fluidized bed as the polymerization reaction zone. Preferred is the process wherein the polymerization reaction is carried out in a vertical cylindrical polymerization reactor containing a fluidized bed of polymer particles supported above a perforated plate, the fluidization grid, by a flow of fluidization gas.

The gas employed to fluidize the bed comprises the monomer or monomers to be polymerized, and also serves as a heat exchange medium to remove the heat of reaction from the bed. The hot gases emerge from the top of the reactor, normally via a tranquilization zone, also known as a velocity reduction zone, having a wider diameter than the fluidized bed and wherein fine particles entrained in the gas stream have an opportunity to gravitate back into the bed. It can also be advantageous to use a cyclone to remove ultra-fine particles from the hot gas stream. The gas is then normally recycled to the bed by means of a blower or compressor and one or more heat exchangers to strip the gas of the heat of polymerization.

A preferred method of cooling of the bed, in addition to the cooling provided by the cooled recycle gas, is to feed a volatile liquid to the bed to provide an evaporative cooling effect. The volatile liquid employed in this case can be, for example, a volatile inert liquid, for example, a saturated hydrocarbon having about 3 to about 8, preferably 4 to 6, carbon atoms. In the case that the monomer or comonomer itself is a volatile liquid or can be condensed to provide such a liquid, this can be suitably be fed to the bed to provide an evaporative cooling effect. Examples of olefin monomers which can be employed in this manner are olefins containing from about 3 to about eight, preferably from 3 to six carbon atoms. The volatile liquid evaporates in the hot fluidized bed to form gas which mixes with the fluidizing gas. If the volatile liquid is a monomer or comonomer, it may undergo some polymerization in the bed. The evaporated liquid then emerges from the reactor as part of the hot recycle gas, and enters the compression/heat exchange part of the recycle loop. The recycle gas is cooled in the heat exchanger and, if the temperature to which the gas is cooled is below the dew point, liquid will precipitate from the gas. This liquid is desirably recycled continuously to the fluidized bed. It is possible to recycle the precipitated liquid to the bed as liquid droplets carried in the recycle gas stream, as described, for example, in EP-A-89691, U.S. Pat. No. 4,543,399, WO 94/25495 and U.S. Pat. No. 5,352,749, which are hereby incorporated by reference. A particularly preferred method of recycling the liquid to the bed is to separate the liquid from the recycle gas stream and to reinject this liquid directly into the bed, preferably using a method which generates fine droplets of the liquid within the bed. This type of process is described in WO 94/28032, the teachings of which are also hereby incorporated by reference.

The polymerization reaction occurring in the gas fluidized bed is catalyzed by the continuous or semi-continuous addition of catalyst. Such catalyst can be supported on an inorganic or organic support material if desired. The catalyst can also be subjected to a prepolymerization step, for example, by polymerizing a small quantity of olefin monomer in a liquid inert diluent, to provide a catalyst composite comprising catalyst particles embedded in olefin polymer particles.

The polymer is produced directly in the fluidized bed by catalyzed (co)polymerization of the monomer(s) on the fluidized particles of catalyst, supported catalyst or prepolymer within the bed. Start-up of the polymerization reaction is achieved using a bed of preformed polymer particles, which, preferably, is similar to the target polyolefin, and conditioning the bed by drying with a dry inert gas such as nitrogen prior to introducing the catalyst, the monomer(s) and any other gases which it is desired to have in the recycle gas stream, such as a diluent gas, hydrogen chain transfer agent, or an inert condensable gas when operating in gas phase condensing mode. The produced polymer is discharged continuously or discontinuously from the fluidized bed as desired, optionally exposed to a catalyst kill and optionally pelletized.

For polymerization of higher olefins such as propylene to produce polypropylene slightly different reaction conditions may be employed. The polymerization is generally conducted under continuous or semicontinuous slurry polymerization conditions in hydrocarbons such as propylene, propane, butene, butane, pentane, butene-2, isobutane, hexane, heptane, and mixtures of the foregoing, generally at temperatures from 50 to 100° C., and pressures from atmospheric to 1 MPa. The polymerization may be conducted in one or more continuous stirred tank tubular reactors or fluidized bed, gas phase reactors, connected in series or parallel. Condensed monomer or solvent may be added to the gas phase reactor as is well known in the art. The catalyst may also be supported and/or prepolymerized prior to use.

In a continuous reaction system, the reaction mixture is typically maintained at conditions at which the polymer is produced as a slurry of powder in the reaction mixture. Use of highly active and highly stereospecific catalyst systems in propylene polymerization substantially eliminates the need to remove catalyst components or atactic polymer from the polymer product. The mixture of reaction components is fed continuously or at frequent intervals into the reactor system and is continuously monitored so as to ensure an efficient reaction and the desired product. For example, it is well known that supported coordination catalysts and catalyst systems of the type described above are highly sensitive, in varying degrees, to catalyst poisons such as water, oxygen, carbon oxides, acetylenic compounds and sulfur compounds. Introduction of such compounds may result in reactor upset and production of off-grade product. Typically, computer control systems are used to maintain process variables within acceptable limits, often by measuring polymer variables such as viscosity, density and tacticity, or catalyst productivity.

In the process, reactants and diluents, which may be a mixture of propylene, hydrogen, nitrogen, unreacted comonomers and inert hydrocarbons, are continuously recycled through the reactor, optionally with scavenging to remove impurities and condensation to remove the heat of polymerization. Catalyst and cocatalysts, fresh monomer or comonomer(s) and selectivity control agents, branching agents or chain transfer agents, if desired, are likewise continuously fed to the reactor. The polymer product is continuously or semi-continuously removed and volatile components removed and recycled. Suitable processes for preparing polypropylene polymers are known in the art and illustrated by those taught in U.S. Pat. Nos. 4,767,735, 4,975,403, and 5,084,513, among others.

Utilizing the catalysts of the present invention, copolymers having high comonomer incorporation and correspondingly low density, yet having a low melt index, may be readily prepared. That is, high molecular weight polymers are readily attained by use of the present catalysts, even at elevated reactor temperatures. This result is highly desirable because the molecular weight of α-olefin copolymers can be readily reduced by the use of hydrogen or similar chain transfer agent, however increasing the molecular weight of α-olefin copolymers is usually only attainable by reducing the polymerization temperature of the reactor. Disadvantageously, operation of a polymerization reactor at reduced temperatures significantly increases the cost of operation since heat must be removed from the reactor to maintain the reduced reaction temperature, while at the same time heat must be added to the reactor effluent to vaporize the solvent. In addition, productivity is increased due to improved polymer solubility, decreased solution viscosity, and a higher polymer concentration. Utilizing the present catalysts, α-olefin homopolymers and copolymers having densities from 0.85 g/cm$^3$ to 0.96 g/cm$^3$, and melt flow rates from 0.001 to 1000 dg/min are readily attained in a high temperature process.

The catalyst system may be prepared as a homogeneous catalyst by addition of the requisite components to a solvent in which polymerization will be carried out by solution polymerization procedures. The catalyst system may also be prepared and employed as a heterogeneous catalyst by adsorbing the requisite components on a catalyst support material such as silica, alumina, aluminosilicates, or other suitable inorganic support material, or a polymer, such as preformed olefin polymer. A preferred support material is silica that has been heated (calcined) to 200 to 800° C. for a time sufficient to remove substantially all surface water and thereafter reacted with a Lewis acid, especially a $C_{1-6}$ trialkylaluminum compound to react substantially all available hydroxyl groups. The heterogeneous form of the catalyst system is employed in a slurry polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the α-olefin monomer or a mixture of different α-olefin monomers may be used in whole or part as the diluent. Most preferably the diluent comprises in at least major part the α-olefin monomer or monomers to be polymerized.

The polymerization may be carried out as a batchwise or a continuous polymerization process A continuous process is preferred, in which event catalyst, α-olefin, and optionally solvent and diene are continuously supplied to the reaction zone and polymer product continuously removed therefrom.

EXAMPLES

It is understood that the present invention is operable in the absence of any component which has not been specifically disclosed. The following examples are provided in order to further illustrate the invention and are not to be construed as limiting. Unless stated to the contrary, all parts and percentages are expressed on a weight basis. The term "overnight", if used, refers to a time of approximately 16–18 hours, "room temperature", if used, refers to a temperature of about 20–25° C., and "mixed alkanes" refers to a mixture of hydrogenated propylene oligomers, mostly $C_6$–$C_{12}$ isoalkanes, available commercially under the trademark Isopar E™ from Exxon Chemicals Inc.

Tris(perfluorophenyl)borane $(C_6F_5)_3B$ (FAB) was obtained as a solid from Boulder Scientific Inc. and further purified by recrystallization from hexane. Rac-dimethylsilane-bis(indenyl- 1-yl)zirconium dichloride was purchased from Boulder Scientific Inc. and the corresponding dimethyl complex was prepared from reaction of the dichloride with two equivalents of MethylMgBr in diethyl ether and purified by recrystallization from a mixture of solvents of toluene and hexane at −35° C. Tris (perfluorophenyl)aluminum $(C_6F_5)_3Al$ (FAAL, as a toluene adduct or solvate free FAAL) was prepared by exchange reaction between tris(perfluorophenyl)borane and trimethylaluminum, substantially as reported by Biagini et.al., U.S. Pat. No. 5,602,269. All solvents were purified using the technique disclosed by Pangborn et al, *Organometallics*, 15, 1518–1520, (1996). All compounds, solutions, and reactions were handled under an inert atmosphere (dry box). All chemical shifts for $^{19}F$ NMR spectra were relative to a fixed external standard ($CFCl_3$) in benzene-$d_6$ or toluene-$d_8$, both of which were dried over Na/K alloy and filtered or distilled prior to use. $^1H$ and $^{13}C$ NMR shifts were referenced to internal solvent resonances and are reported relative to TMS.

Example 1

Rac-dimethylsilanebis(indenyl-1-yl)zirconium bis [($\mu$-methyl)tris(pentafluorophenyl)aluminum]

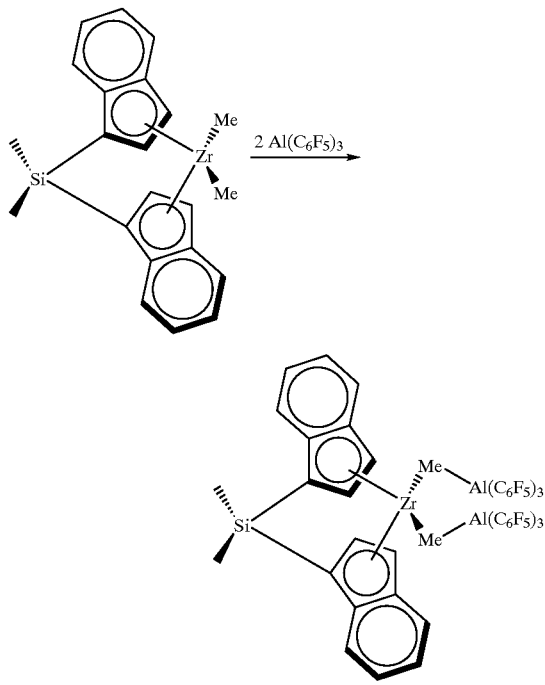

NMR reactions were carried out in J-Young NMR tubes or NMR tubes with good seals, and the samples were loaded into the NMR tubes in a glove box after mixing the above two reagents (rac-dimethylsilanebis(indenyl-1-yl)zirconium dimethyl and FAAL) in 0.7 mL of benzene-$d_6$ in a 1:2 ratio (0.02 mmol scale). The mixture was allowed to react at room temperature for 10 min before the NMR spectra were recorded. A deep red solution was observed immediately after the mixing and the NMR data are consistent with the structure shown in the above equation. This species has a half-life of about 3 h at room temperature. Large crystals are prepared by repeating the above procedure using toluene, cooling the solution to −35° C., and drying choice crystals under inert atmosphere at room temperature. The resulting ORTEP drawing prepared from the single crystal X-ray diffraction analysis data is provided in FIG. 1.

Spectroscopic data for rac-Me$_2$Si($\eta^5$-Ind)$_2$Zr[($\mu$-Me)Al $(C_6F_5)_3]_2$ are as follows. $^1H$ NMR ($C_6D_6$, 23° C.): δ 7.32 (d, $J_{H-H}$=8.7 Hz, 2H, $C_6$-ring H), 6.80 (d, $J_{H-H}$=8.7 Hz, 2H), $C_6$-ring H), 6.65 (d, $J_{H-H}$=3.3 Hz, 2H, $C_5$-ring H), 6.45 (t, $J_{H-H}$=7.5 Hz, 2H, $C_6$-ring H), 6.33 (t, $J_{H-H}$=7.5 Hz, 2H, $C_6$-ring H), 5.40 (d, $J_{H-H}$=3.3 Hz, 2H, $C_5$-ring H), 0.34 (s, 6H), SiMe$_2$), −0.54 (s br, 6H, Al-$\mu$-Me). $^{19}F$ NMR ($C_6D_6$, 23° C.): δ −123.23 (d, $^3J_{F-F}$=15.3 Hz, 12F, o-F), −152.22 (s br, 6F, p-F), −161.09 (s br, 12F, m-F). $^{13}C$ NMR ($C_6D_6$, 23° C.): δ 150.29 (d, $J_{C-F}$=230.8 Hz), 141.48 (d, $J_{C-F}$= 250.7 Hz), 133.87 (d, $J_{C-F}$=266.3 Hz), and 132.09 for $C_6F_5$ groups, 129.28, 128.96, 128.50, 126.00, 125.61, 124.92, 120.25, 114.86, 88.20 for Indenyl groups, 21.36 (Zr-Me-Al), −3.04 (SiMe$_2$).

Example 2

Reaction of rac-dimethylsilanebis(indenyl-1-yl) zirconium dimethyl With Two Equivalents of tris (pentafluorophenyl)aluminum, 20 Hour Study

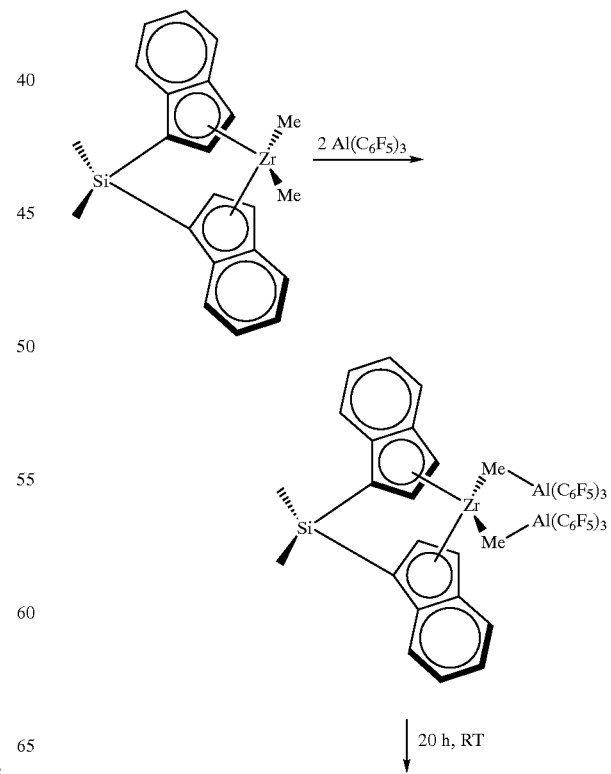

-continued

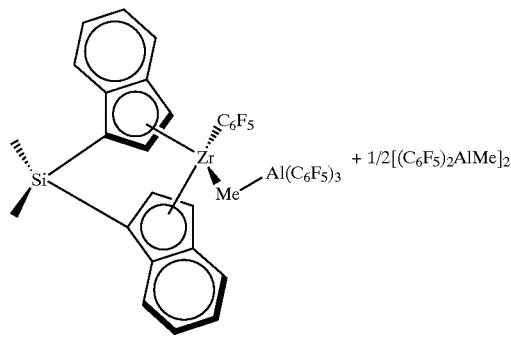

NMR reactions were carried out in J-Young NMR tubes or NMR tubes with good seals, and the samples were loaded into the NMR tubes in a glove box after mixing the above two reagents (rac-dimethylsilanebis(indenyl-1-yl)zirconium dimethyl and FAAL) in 0.7 mL of benzene-$d_6$ in a 1:2 ratio (0.02 mmol scale). The mixture was allowed to react at room temperature and the reaction was monitored by NMR measurements. The 0.7 mL of benzene-$d_6$ in a 1:2 ratio (0.02 mmol scale). The mixture was allowed to react at room temperature and the reaction was monitored by NMR measurements. The initially formed bis($\mu$-methyl) species rac-Me$_2$Si($\eta^5$-Ind)$_2$Zr[($\mu$-Me)Al(C$_6$F$_5$)$_3$]$_2$ $_2$ was slowly converted over 20 hours to two species Me$_2$Si($\eta^5$-Ind)$_2$Zr(C$_6$F$_5$)($\mu$-Me)Al(C$_6$F$_5$)$_3$ and [(C$_6$F$_5$)$_2$AlMe]$_2$ shown in the above equation.

Spectroscopic data for Me$_2$Si($\eta^5$-Ind)$_2$Zr(C$_6$F$_5$)($\mu$-Me)Al(C$_6$F$_5$)$_3$ are as follows. $^1$H NMR (C$_6$D$_6$, 23° C.): δ 7.10–6.98 (m, 4H, Ind), 6.77 (m, 2H, Ind), 6.44 (t, $J_{H-H}$=7.2 Hz, 1H, Ind), 6.24 (m, 2H, Ind), 5.89 (t, $J_{H-H}$=7.2 Hz, 1H, Ind), 5.66 (d, $J_{H-H}$=3.3 Hz, 2H, Ind), 0.42 (s, 3H, SiMe$_2$), 0.37 (s, 3H, SiMe$_2$), −0.58 (d, $J_{H-F}$=3.3 Hz, 3H, Al-$\mu$-Me). $^{19}$F NMR (C$_6$D$_6$, 23° C.): δ −111.15 (d, $^3J_{F-F}$=22.5 Hz, 1F, C$_6$F$_5$), −114.56 (d, $^3J_{F-F}$=22.5 Hz, 1F, C$_6$F$_5$), −122.87 (d, $^3J_{F-F}$=20.5 Hz, 6F, o-F), −152.39 (t, $^3J_{F-F}$=18.3 Hz, 1F, C$_6$F$_5$), −153.80 (t, $^3J_{F-F}$=21.4 Hz, 3F, p-F), −160.62 (t, $^3J_{F-F}$=21.5 Hz, 1F, C$_6$F$_5$), −161.86 (t, $^3J_{F-F}$=19.5 Hz, 6F, m-F), −162.92 (t, $^3J_{F-F}$=11.3 Hz, 1F, C$_6$F$_5$). Spectroscopic data for [(C$_6$F$_5$)$_2$AlMe]$_2$ are as follows. $^1$H NMR (C$_6$D$_6$, 23° C.): δ −0.10 (s br, 3H, Al-Me). $^{19}$F NMR (C$_6$D$_6$, 23° C.): δ −122.24 (s br, 4F, o-F), −151.34 (s br, 2F, p-F), −160.76 (s br, 4F, m-F).

Comparative 1

Reaction of rac-dimethylsilanebis(indenyl-1-yl) zirconium dimethyl With One Equivalent of tris (pentafluorophenyl)aluminum NMR reactions were carried out in J-Young NMR tubes or NMR tubes with good seals, and the samples were loaded into the NMR tubes in a glove box after mixing the above two reagents (rac-dimethylsilanebis(indenyl-1-yl)zirconium dimethyl and FAAL) in 0.7 mL of benzene-$d_6$ in a 1:1 ratio (0.02 mmol scale). The mixture was allowed to react at room temperature for 15 min before the NMR spectra were recorded. A yellow solution was observed and the NMR data are consistent with the structure shown in the above equation. This species has a half-life of about 16 days at room temperature.

Spectroscopic data for Me$_2$Si($\eta^5$-Ind)$_2$ZrMe($\mu$-Me)Al(C$_6$F$_5$)$_3$ are as follows. $^1$H NMR (C$_6$D$_6$, 23° C.): δ 7.55 (d, $J_{H-H}$=8.7 Hz, 1H, Ind), 7.19 (d, $J_{H-H}$=8.7 Hz, 1H, Ind), 7.04 (m, 2H, Ind), 6.93 (d, $J_{H-H}$=8.7 Hz, 1H, Ind), 6.75 (d, $J_{H-H}$=8.7 Hz, 1H, Ind), 6.65 (t, $J_{H-H}$=7.5 Hz, 1H, Ind), 6.53 (s br, 1H, Ind), 6.44 (t, $J_{H-H}$=7.5 Hz, 1H, Ind), 6.36 (t, $J_{H-H}$=7.5 Hz, 1H, Ind), 5.61 (d, $J_{H-H}$=3.2 Hz, 1H, Ind), 5.06 (d, $J_{H-H}$=3.2 Hz, 1H, Ind), 0.36 (s, 3H, SiMe$_2$), 0.26 (s, 3H, SiMe$_2$), −0.71 (s, 3H, Zr-Me), −0.96 (s br, 3H, Al-$\mu$-Me). $^{19}$F NMR (C$_6$D$_6$, 23° C.): δ −122.87 (d, $^3J_{F-F}$=15.3 Hz, 6F, o-F), 153.93 (t, $^3J_{F-F}$=17.2 Hz, 3F, p-F), −161.83 (t, $^3J_{F-F}$=18.3 Hz, 6F, m-F). $^{13}$C NMR (C$_6$D$_6$, 23° C.): δ 150.29 (d, $J_{C-F}$=230.8 Hz), 141.48 (d, $J_{C-F}$=250.7 Hz), 133.87 (d, $J_{C-F}$=266.3 Hz), and 132.09 for C$_6$F$_5$ groups, 129.26, 128.50, 127.39, 127.14, 126.67, 126.44, 126.20, 125.62, 124.98, 123.78, 120.97, 117.68, 115.17, 112.56, 87.54 for Indenyl groups, 48.74 (q, $J_{C-H}$=120.9 Hz, Zr-Me), 10.03 (Zr-Me-Al), −2.35, −3.13 (SiMe$_2$).

Comparative 2

Reaction of rac-dimethylsilanebis(indenyl-1-yl) zirconium dimethyl With One and Two Equivalents of tris(pentafluorophenyl)borane

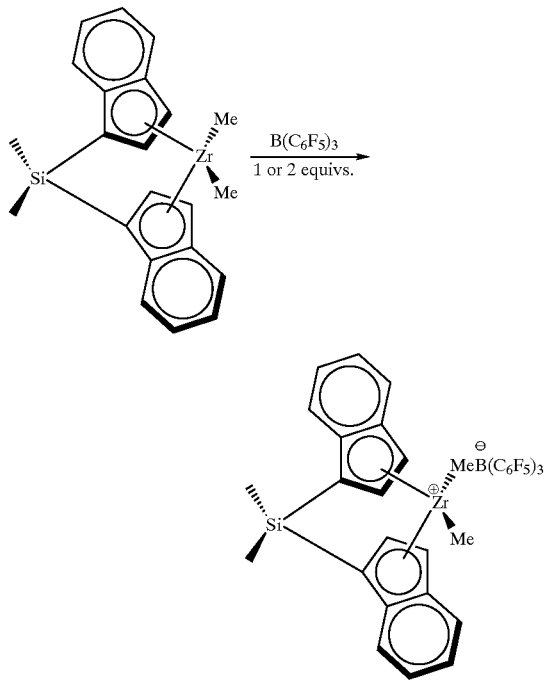

NMR reactions were carried out in J-Young NMR tubes or NMR tubes with good seals, and the samples were loaded into the NMR tubes in a glove box after mixing the above two reagents (rac-dimethylsilanebis(indenyl-1-yl)zirconium dimethyl and FAB) in 0.7 mL of benzene-d$_6$ in proper ratios (1:1 and 1:2, 0.02 mmol scale). The mixture was allowed to react at room temperature for 15 min before the NMR spectra were recorded. A yellow-orange colored solution was obtained and the NMR data are consistent with the structure as shown in the above equation. In the 1:2 ratio reaction, the identical product was produced and the other equivalent of FAB was left unreacted.

Spectroscopic data for Me$_2$Si($\eta^5$-Ind)$_2$ZrMe$^+$[MeB (C$_6$F$_5$)$_3$]$^+$ are as follows. $^1$H NMR (C$_6$D$_6$, 23° C.): δ 7.50 (d, $J_{H-H}$=8.7 Hz, 1H, Ind), 7.05 (m, 2H, Ind), 6.90 (d, $J_{H-H}$=8.7 Hz, 1H, Ind), 6.72–6.58 (m, 4H, Ind), 6.29 (m, 1H, Ind), 6.21 (d, $J_{H-H}$=3.2 Hz, 1H, Ind), 5.67 (d, $J_{H-H}$=3.2 Hz, 1H, Ind), 4.99 (d, $J_{H-H}$=3.2 Hz, 1H, Ind), 0.36 (s, 3H, SiMe$_2$), 0.22 (s, 3H, SiMe$_2$), −0.45 (s br, 3H, B-μ-Me), −0.51 (s, 3H, Zr-Me). $^{19}$F NMR (C$_6$D$_6$, 23° C.): δ −133.55 (d, $^3J_{F-F}$=21.2 Hz, 6F, o-F), −159.32 (t, $^3J_{F-F}$=21.4 Hz, 3F, p-F), −164.45 (t, $^3J_{F-F}$=19.5 Hz, 6F, m-F).

Polymerizations

All liquid and gas feeds were passed through columns of alumina and a decontaminant (Q-5™ catalyst available from Englehardt Chemicals Inc.) prior to introduction into the reactor. Catalyst components are handled in a glovebox containing an atmosphere of argon or nitrogen. A stirred 2.0 liter reactor is charged with about 740 g of mixed alkanes solvent and 120 g of 1-octene comonomer. Hydrogen is added as a molecular weight control agent by differential pressure expansion from a 75 mL addition tank at 25 psi (2070 kPa). The reactor is heated to the polymerization temperature of 130° C. and saturated with ethylene at 500 psig (3.4 MPa). Rac-dimethylsilanebis(indenyl-1-yl) zirconium dimethyl and FAAL, as dilute solutions in toluene, were mixed and transferred to a catalyst addition tank and injected into the reactor. The polymerization conditions were maintained for 15 minutes with ethylene added on demand. The resulting solution was removed from the reactor, quenched with isopropyl alcohol, and stabilized by addition of 10 ml of a toluene solution containing approximately 67 mg of a hindered phenol antioxidant (Irganox™ 1010 from Ciba Geigy Corporation) and 133 mg of a phosphorus stabilizer (Irgafos 168 from Ciba Geigy Corporation).

Between polymerization runs a wash cycle in which 850 g of mixed alkanes is added to the reactor and the reactor heated to 150° C. was conducted. The reactor was then emptied of the heated solvent immediately before beginning a new polymerization run.

Polymers were recovered by drying in a vacuum oven set at 140° C. for about 20 hours. Density values are derived by determining the polymer's mass when in air and when immersed in methylethyl ketone. Micro melt index values (MMI) are obtained using a Custom Scientific Instrument Inc. Model CS-127MF-015 apparatus at 190° C., and are unit-less values calculated as follows:

MMI=1/(0.00343 t−0.00251), where t=time in seconds as measured by the instrument. Results are contained in Table 1.

TABLE 1

| Run | catalyst/activator[1] | ΔT (° C.) | Yield (g) | Efficiency (g polymer/μg Zr) | Density g/ml | MMI | Mw (10$^3$) | Mw/Mn |
|---|---|---|---|---|---|---|---|---|
| 1 | 0.4/1.6 | 4.4[2] | 46.7 | 1.28 | 0.925 | 26.3 | 49.7 | 1.93 |
| 2 | 0.4/0.8 | 0.4 | 28.9 | 0.79 | 0.927 | 35.3 | 47.6 | 1.80 |
| 3* | 0.4/0.4 | 0.5 | 17.5 | 0.48 | 0.926 | 37.1 | 47.5 | 1.77 |

*comparative, not an example of the invention. In run 3, insufficient FAAL was used. Run 3 did not form a μ-bridged bisadduct.
[1] μmoles/μmoles
[2] manual full cooling used to control exotherm Propylene Homopolymerization The above polymerization conditions were substantially repeated excepting that about 250 g of mixed alkanes solvent and 300 g of propylene are polymerized at a polymerization temperature of 70° C.

Catalyst, dimethylsilanebis(2-methyl-4-phenylindenyl) zirconium 1,4-diphenyl-1,3-butadiene (0.125 μmole) and FAAL cocatalyst (0.25 μmole), as dilute solutions in toluene, were then mixed, transferred to a catalyst addition tank, and injected into the reactor. The polymerization conditions were maintained for 15 minutes. 50.9 g Of isotactic polypropylene product were recovered giving a catalyst efficiency of 4.46 g polymer/μg Zr.

Example 3

In a glove box, FAAL (0.032 mmol, toluene adduct) and diisobutyl(2,6-di-t-butyl-4-methylphenoxy)aluminum, (dibal-bot), 0.008 mmol) were mixed in 0.7 mL of benzene-$d_6$ and the mixture was loaded into a NMR tube. Two new species, isobutyl(pentafluorophenyl)(2,6-ditert-butyl-4-methylphenoxy)aluminum (i-Bu($C_6F_5$)Al(BHT)) and isobutylbis(pentafluorophenyl)aluminum (i-BuAl($C_6F_5$)$_2$), as well as a small amount of bis(pentafluorophenyl)(2,6-ditert-butyl-4-methylphenoxy)aluminum (($C_6F_5$)$_2$Al(BHT)) were found to form from the exchange reaction. No di(isobutyl)(2,6-ditert-butyl-4-methylphenoxy)aluminum reagent remained. Residual FAAL reagent was also present.

iBu($C_6F_5$)Al(BHT) $^1$H NMR ($C_6D_6$, 23° C.): δ 7.10 (s, 2H, Ar), 2.25 (s, 3H, Ar—$CH_3$), 1.89 (septet, $J_{H-H}$=6.6 Hz, 1H, $Me_2CHCH_2$—), 1.50 (s, 18H, tBu), 0.89 (d, $J_{H-H}$=6.6 Hz, 6 H, $Me_2CHCH_2$—), 0.50 (d, $J_{H-H}$=7.2 Hz, 2H, $Me_2CHCH_2$—). $^{19}$F NMR ($C_6D_6$, 23° C.): δ 120.93 (dd, $^3J_{F-F}$=18.3 Hz, 2F, o-F), −149.65 (t, $^3J_{F-F}$=21.4 Hz, 1F, p-F), −159.61 (tt, $^3J_{F-F}$=24.5 Hz, 2F, m-F). IBuAl($C_6F_5$)$_2$ $^1$H NMR ($C_6D_6$, 23° C.): δ 1.89 (overlapping with the above structure, 1H, $Me_2CHCH_2$—), 0.99 (d, $J_{H-H}$=6.6 Hz, 6H, $Me_2CHCH_2$—), 0.55 (s, br, 2H, $Me_2CHCH_2$—). $^{19}$F NMR ($C_6D_6$, 23° C.): δ −121.74 (d, $^3J_{F-F}$=18.3 Hz, 2F, o-F), −151.45 (t, $^3J_{F-F}$=20.9 Hz, 1F, p-F), −161.20 (tt, $^3J_{F-F}$=24.5 Hz, 2F, m-F). ($C_6F_5$)$_2$Al(BHT) $^1$H NMR ($C_6D_6$, 23° C.): δ 7.13 (s, 2H, Ar), 2.28 (s, 3H, Ar—$CH_3$), 1.53 (s, 18H, tBu). $^{19}$F NMR ($C_6D_6$, 23° C.): δ −120.93(overlapping with other species, 2F, o-F), −147.41 (t, $^3J_{F-F}$=21.4 Hz, 1F, p-F), −159.12 (tt, $^3J_{F-F}$=24.5 Hz, 2F, m-F).

The metal complex, rac-dimethylsilyl-bis(1-indenyl) zirconium dimethyl, (8 μmol) was added to the above solution whereupon the resulting mixture immediately turned to deep red color. NMR spectroscopic features of the major product were consistent with a μ-bridged bisadduct of the formula: rac-$Me_2Si(\eta^5$-Ind)$_2Zr[(\mu$-Me)Al($C_6F5)_3]_2$.

Example 4

In a glove box, FAAL (0.032 μmol, toluene adduct) was dissolved in 0.7 mL of benzene-$d_6$ in a J-Young NMR tube and MMAO-3A (4 μmol, FAAL/MMAO=8/1) was added. The NMR spectroscopic features of the product were consistent with a mixture of the formula:

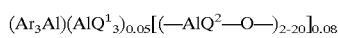

($Q^1$ and $Q^2$=methyl or isopropyl). The metal complex, rac-dimethylsilyl-bis(1-indenyl)zirconium dimethyl, (8 μmol) was added to activator mixture. The resulting mixture immediately turned to a deep red color. NMR spectroscopic features of the major product were consistent with a μ-bridged bisadduct of the formula, rac-$Me_2Si(\eta^5$-Ind)$_2Zr[(\mu$-Me)Al($C_6F_5)_3]_2$.

What is claimed is:

1. An ansa bis(μ-substituted) Group 4 metal and aluminum metallocene compound corresponding to the formula:

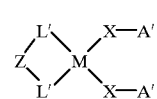

(I)

wherein:

L' independently each occurrence is a π-bonded group,

M is a Group 4 metal,

Z is a divalent bridging group causing the complex to have an ansa structure,

X independently each occurrence is a Lewis basic ligand group able to form a μ-bridging ligand group, and optionally the two X groups may be joined together, and A' independently each occurrence is an aluminum containing Lewis acid compound that forms an adduct with the metal complex by means of the μ-bridging groups, and optionally two A' groups may be joined together thereby forming a single difunctional Lewis acid containing compound.

2. The compound of claim 1 wherein X is selected from the group consisting of hydrocarbyl, silyl, N,N-dialkylamido and alkandiylamido groups of up to 20 atoms not counting hydrogen, or two such X groups together are an alkanediyl or alkenediyl group which together with M form a metallocycloalkane or metallocycloalkene.

3. The compound of claim 1 wherein A' corresponds to the formula:

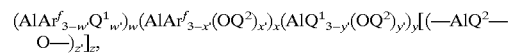

where;

$Ar^f$ is a fluorinated aromatic hydrocarbyl moiety of from 6 to 30 carbon atoms;

$Q^1$ is $C_{1-20}$ alkyl;

$Q^2$ is $C_{1-20}$ hydrocarbyl, optionally substituted with one or more groups which independently each occurrence are hydrocarbyloxy, hydrocarbylsiloxy, hydrocarbylsilylamino, di(hydrocarbylsilyl)amino, hydrocarbylamino, di(hydrocarbyl)amino, di(hydrocarbyl)phosphino, or hydrocarbylsulfido groups having from 1 to 20 atoms other than hydrogen, or, optionally, two or more $Q^2$ groups may be covalently linked with each other to form one or more fused rings or ring systems;

w' is a number from 0 to 3;

w is a number from 0 to 1.0;

x' is a number from 0 to 3;

x is a number from 1.0 to 0;

y' is a number from 0 to 3;

y is a number from 1.0 to 0;

z' is a number from 0 to 30; and z is a number from 0 to 20.

4. The compound of claim 3 wherein the Lewis acid is prepared by exchange tris(pentafluorophenyl)boron and an alkylaluminum- or alkylaluminumoxy-compound.

5. The compound of claim 1 corresponding to the formula:

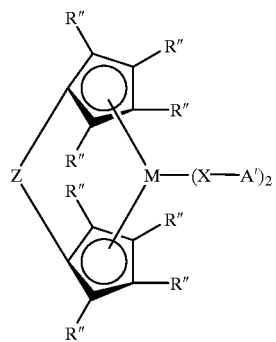

wherein:

R″ in each occurrence independently is selected from the group consisting of hydrogen, hydrocarbyl, silyl, halohydrocarbyl, N,N-dialkylamino, and alkanediylamino, said R″ having up to 20 atoms, not counting hydrogen, or adjacent R″ groups are joined together thereby forming a fused ring system, X independently each occurrence is hydrocarbyl, or two X groups together are an alkanediyl or alkenediyl group, said X having up to 20 atoms not counting hydrogen;

Z is $SiR^*_2$, $CR^*_2$, $SiR^*_2SiR^*_2$, $CR^*_2CR^*_2$, $CR^*=CR^*$, $CR^*_2SiR^*_2$, $BOR^*$, $BNR^*_2$, or $GeR^*_2$, wherein $R^*$ independently each occurrence is $C_{1-4}$ alkyl or $C_{6-10}$ aryl, or optionally two $R^*$ groups are joined together; and M, and A' are as previously defined in claim 1.

6. The compound of claim 1 wherein L' is cyclopentadienyl, tetramethylcyclopentadienyl, indenyl, 2,3-dimethylindenyl, fluorenyl, 2-methylindenyl, 2-methyl-4-phenylindenyl, 3-dimethylaminoindenyl, 3-pyrrolidinoindenyl, 3-piperidinoindenyl, 2-methyl-4-(3,5-bis(trifluoromethyl)phenyl)inden-1-yl, 2,4,6,7-tetramethylinden-1-yl, 2-methyl-4-(1-naphthyl)indene-1-yl, 3,4-cyclopenta(1)phenanthrenyl, 2,3-cyclopenta(1)phenanthrenyl, 2-methyl-4,5-benzoinden-1-yl tetrahydrofluorenyl, octahydrofluorenyl, 1-indacenyl, 3,4-(cyclopenta(l)phenanthren-1-yl), or tetrahydroindenyl.

7. A compound according to claim 1 corresponding to the formula:

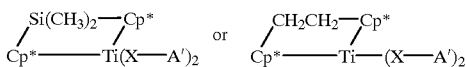

wherein:

Cp* is tetramethylcyclopentadienyl, 2-methyl-4-phenylinden-1-yl, 3-pyrrolidinoinden-1-yl, 1-indacenyl, or 3,4-(cyclopenta(l)phenanthren-1-yl);

X is methyl, and

A' is tris(pentafluorophenyl)aluminum.

8. A process for preparing a metal complex according to claim 1 comprising contacting a charge-neutral Group 4 metal coordination complex having at least two Lewis basic groups corresponding to the formula

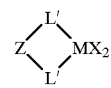

with at least two molar equivalents of charge-neutral aluminum coordination complexes, A', having Lewis acidic aluminum atoms such that at least two of the aluminum atoms of the aluminum coordination complexes bond to at least two of the Lewis basic groups of the Group 4 coordination complex, wherein Z, L', M, X and A' are as defined in claim 1.

9. A process for the polymerization of α-olefins comprising contacting one or more α-olefins with a catalyst composition comprising:

1) a group 4 metal complex corresponding to the formula:

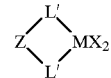

wherein, Z, L', M, and X are as previously defined in claim 1; and 2) tris(perfluorophenyl)aluminum, wherein the equivalent ratio of metal complex:tris(perfluorophenyl)aluminum is from 1:2 to 1:5.

* * * * *